United States Patent
Satake et al.

(10) Patent No.: US 6,466,321 B1
(45) Date of Patent: Oct. 15, 2002

(54) METHOD OF DIAGNOSING NUTRITIOUS CONDITION OF CROP IN PLANT FIELD

(75) Inventors: Satoru Satake, Tokyo; Yukio Hosaka, Hiroshima; Hideharu Maruyama, Hiroshima; Nobuhiko Nakamura, Hiroshima, all of (JP)

(73) Assignee: Satake Corporation, Tokyo (JP)

(*) Notice: Subject to any disclaimer, the term of this patent is extended or adjusted under 35 U.S.C. 154(b) by 312 days.

(21) Appl. No.: 09/595,023

(22) Filed: Jun. 16, 2000

(30) Foreign Application Priority Data

Jun. 17, 1999 (JP) .................................. 11-171712

(51) Int. Cl.⁷ .............................. G01J 3/51; G06K 9/00
(52) U.S. Cl. ....................... 356/402; 356/416; 356/413; 356/419; 382/110
(58) Field of Search .................. 356/402, 416, 356/418, 419; 382/110

(56) References Cited

U.S. PATENT DOCUMENTS

| | | |
|---|---|---|
| 4,371,081 A | 2/1983 | Satake |
| 4,429,225 A | 1/1984 | Fumoto et al. |
| 4,630,736 A | 12/1986 | Maughan et al. |
| 4,699,274 A | 10/1987 | Saika |
| 4,742,228 A | 5/1988 | Bischoff |
| 4,801,804 A | 1/1989 | Rosenthal |
| 5,135,114 A | 8/1992 | Satake et al. |
| 5,220,400 A | 6/1993 | Anderson et al. |
| 5,254,858 A | 10/1993 | Wolfman et al. |
| 5,258,825 A | 11/1993 | Reed et al. |
| 5,443,164 A | 8/1995 | Walsh et al. |
| 5,638,961 A | 6/1997 | Satake et al. |
| 5,735,402 A | 4/1998 | Pezzoli et al. |
| 6,160,902 A * | 12/2000 | Dickson et al. ............. 382/110 |
| 6,178,253 B1 * | 1/2001 | Hendrickson et al. ...... 382/110 |
| 6,366,681 B1 * | 4/2002 | Hutchins .................... 382/110 |

FOREIGN PATENT DOCUMENTS

| | | |
|---|---|---|
| EP | 0443769 A2 | 8/1991 |
| EP | 0727260 | 8/1996 |
| EP | 0834731 A2 | 4/1998 |
| JP | 08015141 A | 1/1996 |

OTHER PUBLICATIONS

Nippon Shokuhin Kogyo Gakkaishi, "Applicability of Near Infrared Reflectance Method to Moisture, Protein ans Ash Measurements of Buckwheat Flours", 1984, vol. 31, No. 3, pp. 200–202.

Nippon Shokuhin Kogyo Gakkaishi, "Near Infrared Reflectance Analysis for Determining Moisture, Protein and Ash Contents in Home–grown Wheat Flours", 1984, vol. 31, No. 1, pp. 50–53.

* cited by examiner

Primary Examiner—F. L. Evans
(74) Attorney, Agent, or Firm—Fish & Richardson P.C.

(57) ABSTRACT

From the crop of a predetermined area in a plant field under exposure to natural light, a reflectivity of the light having relation to crop information such as nitrogen content rate is measured by a camera; the crop information as first crop information is obtained from the first crop related formula established in advance for obtaining the crop information from the reflectivity; light is irradiated on crop leaf blades in the same area as the predetermined area and an amount of the light is measured; the crop information as second crop information is obtained from the second crop related formula established in advance for obtaining the crop information from the amount of the light; differences are calculated from the first crop information and the second crop information; the first crop information is obtained from the unknown crop in the predetermined area within the crop field of the same area; the first crop information is corrected based on the differences; and the nutritious diagnosis of the crop in the field is conducted by the corrected first crop information. In conducting diagnosis of crop by measuring the reflection light amount from the crop, since compensation or correction is performed, no great errors occur caused by differences in the measurement locations and the planting densities, and the diagnosis of the crop is simple and easy and, more over, the precision in the measuring is enhanced.

34 Claims, 10 Drawing Sheets

| NO① 3.8% | NO② 4.0% | NO③ 4.0% |
|---|---|---|
| NO④ 3.6% | NO⑤ 4.2% | NO⑥ 4.0% |
| NO⑦ 3.6% | NO⑧ 4.0% | NO⑨ 3.8% |

| NO① 3.8→2.6 | NO② 4.0→2.8 | NO③ 4.0→2.8 |
|---|---|---|
| NO④ 3.6→2.4 | NO⑤ 4.2→3.0 | NO⑥ 4.0→2.8 |
| NO⑦ 3.6→2.4 | NO⑧ 4.0→2.8 | NO⑨ 3.8→2.6 |

METHOD OF DIAGNOSING NUTRITIOUS CONDITION OF CROP IN PLANT FIELD

BACKGROUND OF THE INVENTION (1) Field of the Invention

The invention relates to a method of diagnosing nutrition of crop by obtaining crop information represented by nitrogen content, etc. of the crop from reflection light of the crop growing in a field.

(2) Description of the Related Art

A first conventional method for obtaining crop information such as a nitrogen content rate of a crop, a leaf color value, a nitrogen absorption amount, a plant height, a dry matter weight, etc., is one in which the amount of reflection light from the reference plate and that from the crop in the field is obtained by image-taking, by a light receiving means such as a digital camera, the reference plate which is coated with barium sulfate, etc. and the unit field (or a part of it) in which the crop grows, the reflectivity of the crop is obtained from the amount of the light reflected from the reference plate and the crop, and the nitrogen content rate (amount of nitrogen absorption, a value of leaf color, a plant height, a dry matter weight) is obtained from the reflectivity obtained and the relation formula predetermined for obtaining the nitrogen content rate (amount of nitrogen absorption, a value of leaf color, a plant height, a dry matter weight) from the reflectivity, and the growth diagnosis has been conducted by comparing with a standard nitrogen content rate of that time period based on the number of growth days versus the nitrogen amount curve. However, the amount of reflection light of the crop to be obtained from the field is subject to change by weather. Also, even when the weather is compensated by the reference plate, it is necessary that each of the measuring direction, wind, and planting density be in the same condition as that applied when the predetermined relation formula was prepared for obtaining the nitrogen content rate from the reflectivity. When the condition is different, the compensation is necessary accordingly, so that it cannot be said that all has been compensated only by obtaining the reflectivity by the reference plate as reference. Actually, the measurement has been conducted under the limitation by the solar height, measuring direction, planting density or kind.

As for a second conventional method for obtaining crop information, there is an apparatus in which the light with a wavelength having relation to the crop information subject to increase or decrease depending on the growth of the crop, for example, the light ranging from a visible light region to a near infrared region is irradiated on a leaf blade of the crop and, based on the amount of the received light obtained with respect to the light with the wavelength having relation to the crop information and on the nitrogen amount related formula predetermined for calculating from the amount of light received, for example, a leaf blade nitrogen content, the leaf blade nitrogen content is measured. This apparatus is used to measure a number of the leaf blades of the crop in the field and has enabled to obtain the leaf blade nitrogen content with a high precision. However, in order to grasp the crop information accurately for the overall field, a minute measurement to extend to the overall field was indispensable, which is complicated and troublesome.

The first conventional method described above is one in which, although the measurement is simple, the crop information to be obtained from the field is influenced by factors such as a measuring location and a planting density and, because of constraint in the measuring time and location, the method cannot be regarded as accurate. The second method, having no restraint in the measurement and having a high precision, is more advantageous than the first method. However, the problems in the second method are that the measurement has to be made for each leaf blade, thus requiring a large number of points to be measured and a long time accordingly.

SUMMARY OF THE INVENTION

An object of the present invention is that, when obtaining the crop information by measuring the amount of reflection light, the compensation can be made so that no large error occurs caused by the measuring locations and the planting densities, and a method of diagnosing nutrition of the crop provided is simple and easy in the measurement of the crop information and enhances the measurement precision.

A first method of the invention is a method of diagnosis for crop in a field in which, from crop in a fixed area in a crop field under exposure to the natural light, reflectivity of light with a wavelength having relation to crop information which increases or decreases depending on growth of the crop is measured; crop information of a predetermined area from said reflectivity and a first crop related formula predetermined from reflectivity for obtaining crop information is obtained and stored as first crop information; an amount of at least either of transmission light or reflection light with a wavelength having relation to the crop information which increases or decreases depending on growth of the crop is measured; crop information from said amount of light and a second crop related formula predetermined from an amount of light for obtaining crop information is obtained and stored as second crop information; a difference between said first crop information and said second crop information is obtained; the first crop information is obtained from the unknown crop of a predetermined area in the same field; the first crop information is compensated based on said difference; and the nutritious diagnosis of the crop in the field is made based on said first compensated crop information.

The obtaining of the first crop related formula by obtaining the reflectivity obtained from the amount of reflection light of the crop and the amount of reflection light for obtaining the first crop information in advance has been subject of research and is conventional, and also the obtaining of the second crop related formula for obtaining the second crop information determined by obtaining the reflectivity by irradiating light on leaves has also been subject of research and is conventional. Therefore, such information can readily be obtained. According to the invention, and the two useful means mentioned above are effectively combined, the difference between the first crop information and the second crop information respectively obtained from the two means is calculated. By using this difference for compensating the first crop information, it is possible to compensate not only the errors caused by weather changes (weather, time, solar position) but also the errors caused by changes in cultivation factors (measuring direction, planting density) which have heretofore been considered difficult to be compensated. This method is especially suited for conducting nutrition diagnosis at a plurality of spots in the same field because the compensation can be performed simply and easily.

Where the difference between the first crop information and the second crop information decided as above is stored, only by obtaining the first crop information from the unknown crop in the fixed area in the field from which the first crop information has been obtained, it is possible to compensate the first crop information by the first crop information and the above difference. This method enables the easy compensation of the errors caused by the planting density and the measuring direction, and the method may be embodied in an apparatus with the compensation value being provided. Such apparatus can be readily used for crop nutrition diagnosis.

A second invention relates to a method of diagnosis for crop in which, from the crop in the fixed area in a field under exposure to the natural light, the reflectivity of light which has wavelength having relation to the crop information subject to increase or decrease depending on the growth of the crop is measured; crop information for each division is calculated based on the reflectivity for each division of a plurality of divisions and the first crop related formula predetermined for obtaining the crop information from the reflectivity, and such information is made the first crop information and stored; the crop information of at least two divisions from the first crop information stored for each division is selected; light is irradiated on the leaf blade falling within the two divisions of the field; at least either of the transmission light or reflection light which has wavelength having relation to the crop information subject to increase or decrease depending on the growth of the crop is measured; crop information of the two divisions is calculated from said amount of light and the crop related formula predetermined for obtaining the crop information from the amount of light and such information is made the second crop information and stored; a compensation conversion formula for compensating the first crop information based on the second crop information is determined; the first crop information is compensated for each division by the compensation conversion formula and is made the third crop information; and the nutritious diagnosis of the crop in the plant field is made by the resulting third crop information.

For conducting a more strict compensation than in the first crop nutrition diagnosing method, the second crop nutrition diagnosing method is applied. That is, after the crop information is obtained and divided into a plurality of divisions, at least two points of data from within the plurality of divisions are selected, and the second crop information is obtained directly from the crop leaves in the same field as the field from which the two points of data are selected. Thus, from the two points of data of the first and the second crop information, the correlation thereof is determined and the compensation related formula is defined and, based on this formula, all the values in the plurality of divisions are compensated. In obtaining the compensation related formula, the plurality of crop information can be obtained from the fixed extent of area and, further, from the compensation related formula, the first crop information can be compensated for a large extent of area.

In the first and the second nutrition diagnosing methods explained above and the crop diagnosis to which such methods are applied, the first crop information may be obtained for each unit crop field, or may be obtained for each unit area which is arbitrary determined and which is smaller than the unit crop field. The unit crop field here refers to one field divided by what is normally called "furrow".

A third invention relates to a method of diagnosis for crop in which, from the crop in each division of a plurality of divisions in a field exposed to the natural light, the reflectivity of light which has wavelength having relation to the crop information subject to increase or decrease depending on the growth of the crop is measured; the crop information for each division is calculated from the reflectivity and the first crop related formula predetermined for obtaining the crop information from the reflectivity and such information is made the first crop information and stored; the crop information of at least two divisions from the first crop information stored for each division is selected; light is irradiated on the leaf blade falling within the two divisions of the field; at least either of the transmission light or reflection light which has wavelength having relation to the crop information subject to increase or decrease depending on the growth of the crop is measured; crop information of the two divisions is calculated from said amount of light and the crop related formula predetermined for obtaining the crop information from the amount of light and such information is made the second crop information and stored; a compensation conversion formula for compensating the first crop information based on the second crop information is determined; the first crop information is compensated for each division by the compensation conversion formula and is made the third crop information; and the nutritious diagnosis of the crop field is made by the resulting third crop information.

Unlike the above second crop diagnosing method, the third method obtains the information relating to the plurality of divisions individually. The data of at least two divisions are selected from among the plurality of divisions and, by obtaining the second crop information directly from the crop leaves in the same divisions as those of the data in the two divisions, the correlation between the first crop information and the second crop information is determined by the data of the two points and the compensation related formula is defined. Based on this formula, all the values of the plurality of divisions can be compensated. In obtaining the compensation related formula, the plurality of crop information can be obtained from a large extent of area and, further, from the compensation related formula, the first crop information can be compensated for a large extent of area.

As to the division in the third crop diagnosing method, the unit crop field may be formed of one division, the first crop information may be obtained from a plurality of unit crop fields, or the first crop information may be obtained in each division from a plurality of divisions set within the unit crop field.

In the second and third crop diagnosing methods described above, the first crop related formula and the compensation conversion formula are stored and the reflectivity from the crop leaves of unknown fields is measured whereby, based on the first crop related formula and the compensation conversion formula, the third crop information can be obtained. Where these items are stored in a memory section of a control means and are used for appropriate operation, the method can be realized as an apparatus which, not only realizes the diagnosing of the crop but also contributes in enhancing the precision in the measurement.

Concerning the second and the third crop diagnosing methods, the arbitrary two divisions to be selected from among the plurality of divisions may be divisions of the maximum value and the minimum value, respectively, from the first crop information. In this way, the straight line in the compensation conversion of the first crop information and the second crop information can be determined readily at the two points, high and low, without being affected by the remaining data.

There can be various crop information but, for purposes of diagnosing nutrition of the crop, the nitrogen content of leaves or the color values of leaves are considered the best. This is understandable from the fact that, in the crop, the nitrogen content in leaves is the factor which immediately shows the effectiveness of the fertilization or whether the fertilization is appropriate or not.

In the first through third crop diagnosing methods, in order to measure the reflectivity of the light which has wavelength having relation to the crop information subject to increase or decrease depending on the growth of the crop, the reflectivity of the crop is image-taken by the image-taking elements constituted by a plurality of image elements, the image elements having received the reflection light corresponding to the crop are selected, and the reflectivity is measured based on the light received data of the selected image element, thereby providing a method of diagnosing the crop by obtaining the first crop information. The reflection light obtained by an image-taking means such as a digital camera is influenced by the planting density or the dimension of the image-taken field, for example, whether the unit field is within the extent of 1 $m^2$, so that the light image-taken of the crop as the reflection light is not necessarily the reflection light. That is, from the stand point of the unit image element, the reflection light from other than the crop, for example, the light reflected from the soil of the field may be included. Thus, only the image elements which relate to the reflectivity of the predetermined extent of area is selected and is used as the reflection light from the crop, and the first crop information is obtained based on such data of the received light.

BRIEF DESCRIPTION OF THE DRAWINGS

The above and other objects, features and advantages of the present invention will be apparent from the following description of preferred embodiments of the invention explained with reference to the accompanying drawings, in which.

PREFERRED EMBODIMENTS OF THE INVENTION

Figure 1:
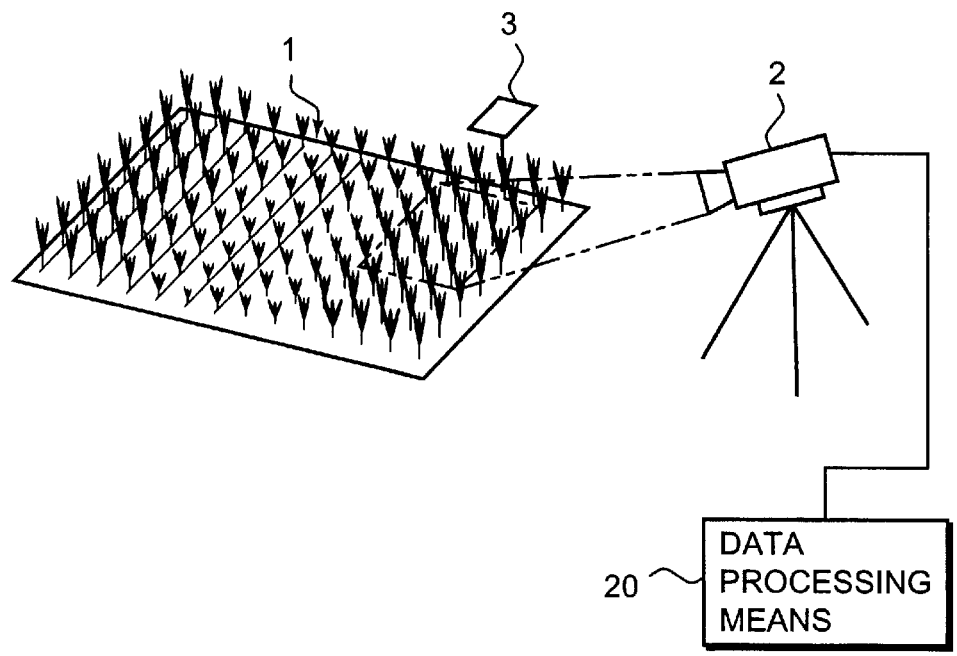
FIG. 1 is a sketch showing locations of a camera and a reference plate disposed in a field for measuring reflection light of crop leaves.

The measuring apparatus according to the present invention is explained with reference to FIG. 1 through FIG. 3. Here, the rice plant is used as an example of crop. A camera 2 which is a light receiving means for measuring reflection light from the crop is directed to a field 1 in which the crop is growing. The field 1 is of course exposed to the natural light. Also, the reference plate 3 in white color is disposed in the crop field 1.

Figure 2:
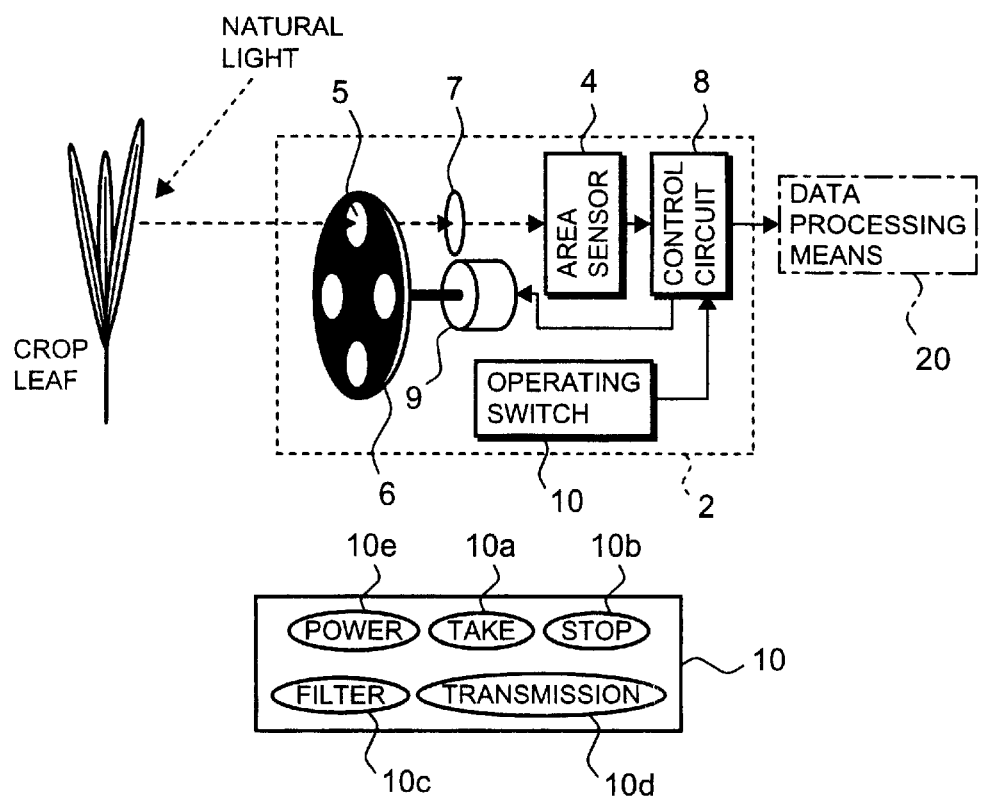
FIG. 2 is a block diagram of the camera for measuring reflection light of the crop leaves.

FIG. 2 is a block diagram showing the camera 2. The camera 2 has a resolution power in the order of 240,000 (600×400) pixels and is equipped with an area sensor 4. In the camera 2, there is a filter wheel 6 equipped with a plurality of narrow band-pass filters 5, and the filters 5 are switched by rotating, for example, the filter wheel 6. The light having passed the filter 5 is received by the area sensor 4 via, for example, a converging lens 7 as an optical means. The filter wheel 6 is rotated by a stepping motor 9 under the control of a control circuit 8. Further, the control circuit 8 forwards a signal of the light received from the sensor 4 to the data processing means 20.

The respective filters 5 are suitably selected from among visible light wavelengths of 450, 550, 625, 650, 675 and 700 nm, and also from among near infrared region wavelengths of 750, 850, 950–1300 nm. As to these wavelengths, it is necessary to select regions which show characteristic changes caused by changes in nitrogen content rates or color values of leaves of the crop. Thus, the filters may be selected from both visible light wavelengths and near infrared region wavelengths, or may be selected from either of them. Further, the wavelengths are not limited to those in the embodiment of the invention. FIG. 2 shows four filters, but the number of filters is not limited and is changeable and may be changed according to the intended purposes. To the control circuit 8 is connected an operating switch 10. The operating switch 10 is equipped with an image-taking starting switch 10a for starting the image-taking operation, an image-taking stopping switch 10b for stopping the image-taking operation, a filter switching switch 10c for switching the filters, a data transmission switch 10d for transmitting the image-taken data, and a power switch 10e.

Figures 3, 4:
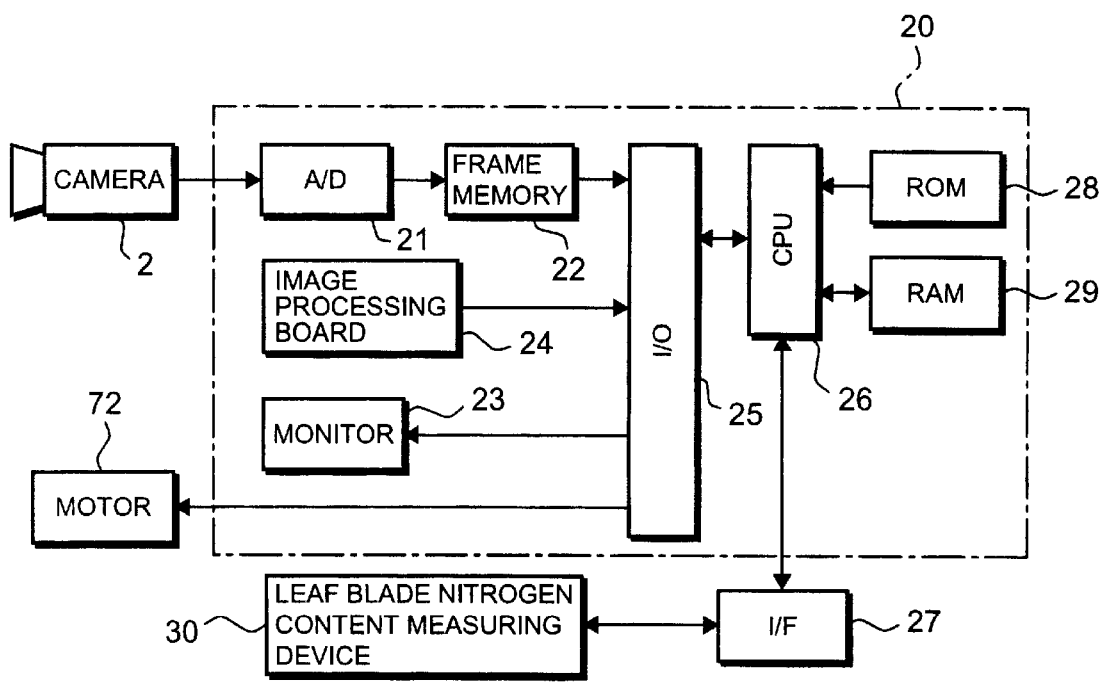
FIG. 3 is a block diagram of a data processing means.
FIG. 4 is a diagram showing a depression angle and a field angle when the crop field is image-taken.

FIG. 3 shows, in a block diagram, a data processing means 20. The data processing means 20 is equipped with an analog/digital converter (hereinafter referred to as "A/D converter") 21, a frame memory 22 for storing image data after the A/D conversion, a monitor 23 for visually showing the image data, and a digital image processing board 24. These are in communication with a CPU 26 which arithmetically processes the image data through an input/output port (hereinafter referred to as "I/O port") 25, and are connected to a leaf blade nitrogen content measuring device 30 explained later via an interface board (hereinafter referred to as "I/F board") 27. Also, to the CPU 26, there are connected a read only memory (hereinafter referred to as "ROM") 28 in which a control program, etc. is stored, and a read and write memory (hereinafter to as "RAM") 29 which enables the storing of the calculated results and the reading of them as desired.

When the power switch 10e of the camera is pressed, the reflection light signal of the image is received by the area sensor 4 and becomes the image signal and, when the data transmission switch 10d is pressed, this image signal is forwarded to the data processing means 20. At the data processing means 20, the image signal is processed by the image processing board 24 and the processed image is displayed on the monitor 23. At the monitor 23, while the field 1 is being confirmed, the location of the camera is set and the extent of the image-taking is determined. Once the extent of the image-taking is determined, the leaves of the rice plant growing in the field 1 are image-taken through the filter 5 presently set by pressing the image-taking starting switch 10a, and then the filter switching switch 10c is switched whereby a signal is outputted from the control circuit 8 for the stepping motor 9 and the filter wheel 6 is rotated. After the switching of the filter 5 by the rotation of the filter wheel 6, the image-taking is again performed through the new filter by pressing the image-taking switch 10a. Consequently, the image signal is produced for each filter 5. Here, if the area sensor 4 of the camera 2 lacks a large capacity of memory elements, the data transmission switch 10d is pressed every time the image is taken for the data to be transmitted to the data processing means 20.

The reflection light amount received by the area sensor 4 of the camera 2 is the reflection light amount of the reference plate 3 and the reflection light amount of the crop leaf in the field 1. When the reflection light amount of the reference plate 3, that is, the reference light amount is measured, the calculation can be made of the amount of light incident by the natural light. That is, if the reference plate 3 is one in which the reflectivity is known, the reflectivity of the reference plate 3 is to be explained as being a fixed reflectivity of, for example, 95%, and the amount of reflected light when the reflected light from the reference plate 3 is measured is assumed to be X and the unknown amount of light of the natural light (reference light amount) is assumed to be Y, the following Formula 1 is established.

$$Y = X/0.95 \tag{1}$$

Y: Amount of natural light (reference light amount)
X: Amount of light from reference plate By the above Formula 1, the amount of light of the natural light (reference light amount) Y can be calculated. Therefore, if the reflection light from the rice crop measured is Z, the following Formula 2 is satisfied.

$$U = Z/Y \tag{2}$$

U: Reflectivity of leaves of rice crop
Y: Amount of natural light (reference light amount)
Z: Amount of reflected light from leaves of rice crop Thus, the reflectivity of rice crop leaves can be obtained. This reflectivity is utilized for calculating the nitrogen content in the rice crop leaves. These Formulas 1 and 2 are stored in the ROM 28. The above mentioned amount of the natural light is measured and stored in the following ways. The filters 5 which the camera 2 is equipped with are switched and the reflection light amount of the reference plate 3 is measured for each filter and the measured data is transmitted to the data processing means 20 where the data is digitally converted by the A/D converter 21 and stored in the RAM 29. That is, the value of the amount of the natural light Y is measured at each filter 5 and is stored.

By the camera 2, the filters 5 are switched and, at each filter, the reflection light amount of the leaves of the rice crop in a certain range in the field 1 is received and transmitted to the data processing means 20. At the data processing means 20, the signal is digitally converted by the A/D converter 21 and is stored in the frame memory 22. At the CPU 26, with respect to the reflection light amount of the leaves at each filter 5 stored in the frame memory 22, the average value of the reflection light amount received by each image element is obtained, and the reflectivity is calculated based on the above mentioned Formula 2 stored in advance in ROM 28 with the calculated result being stored in RAM 29. In this way, the reflectivity of the crop leaves in a certain range, for example, within 1 square meter (1 m$^2$), by unit image element is stored. With respect to the reflectivity obtained here, it is preferable that the difference in the amount of incident light which, in the case where the camera is placed on the ground in substantially the same level as the crop field, occurs because of the difference in the incident angles of the reflection light from the crop field to the camera caused by the far and near relation between the camera and the crop field is compensated.

FIG. 4 shows an example wherein the image data of 240,000 pixels taken from the crop leaves in the field 1 is further divided into a plurality of divisions. For example, by the camera 2, the filters 5 are switched and, at each filter, the reflection light amount of the leaves of the rice crop in a certain range in the field 1 is received and transmitted to the data processing means 20. At the data processing means 20, the signal is digitally converted by the A/D converter 21 and is stored in the frame memory 22. At the CPU 26, with respect to the reflection light amount of the leaves at each filter 5 stored in the frame memory 22, the divisions Nos. ①–⑨, for example, from the left hand top in FIG. 4 are made, and the average value of the reflection light amount received by each image element 2 is obtained. Then, based on the above mentioned Formula 2 stored in advance in ROM 28, the reflectivity for each division of the 9 divisions is calculated and stored in RAM 29. If the extent in which one camera receives the light is assumed to be, for example, 1 m$^2$, the reflectivity of the 9 divisions within 1 m$^2$ is stored. On the monitor 23, the image having been processed by the image processing board 24 is displayed.

In the RAM 29, the reflectivity of the crop leaves within the above certain area of the field received through each of a plurality of filters 5 and the reflectivity of the crop leaves respectively processed in the 9 divisions by each filter 5 are stored. The reflectivity in each filter 5 stored in RAM 29 or the reflectivity processed in the 9 divisions by each filter 5 are made explanatory variables and, by collecting the leaves growing within the same certain range or within the same division, the crop information from these leaves, e.g., the nitrogen content directly and chemically analyzed, or the color value obtained by directly measuring the color of the leaves, the nitrogen content rates or the color values are made objective valuables. Then, the relation formula (first crop related formula) for obtaining the crop information of the crop leaves within the certain range in the field and the relation formula (first crop related formula) for obtaining the crop information of the leaves of the crop for each of the 9 divisions are prepared and stored in ROM 28.

Further, assuming that there exist reflectivity R1 by the filter 1 at the division No. ①, reflectivity R2 by the filter 2, reflectivity R3 by the filter 3, and reflectivity R4 by the filter 4, and there exists a nitrogen content rate N1 obtained by chemically analyzing the crop leaves within the same division, and if the following Formula 3 is satisfied, $$N1 = F0 + F1 \cdot R1 + F2 \cdot R2 + F3 \cdot R3 + F4 \cdot R4, \tag{3}$$

by measuring a plurality of nitrogen content rates N, the following Formula 4 will be established.

$$N1 = F0 + F1 \cdot R11 + F2 \cdot R21 + F3 \cdot R31 + F4 \cdot R41$$

$$N2 = F0 + F1 \cdot R12 + F2 \cdot R22 + F3 \cdot R32 + F4 \cdot R42$$

. . .

$$Nn = F0 + F1 \cdot R1n + F2 \cdot R2n + F3 \cdot R3n + F4 \cdot R4n \tag{4}$$

If the multiple regression analysis is made here, the following Formula 5, namely, the first crop related formula is obtained.

$$N = F0 + F1 \cdot R1 + F2 \cdot R2 + F3 \cdot R3 + F4 \cdot R4 + C \quad (5)$$

wherein, N: Nitrogen content rate of the measured subject
F0~F4: Constant
R1~R4: Reflectivity of each filter
C: Compensation value For leaf color values, too, the related formula may be obtained similarly. The above Formula 5 is stored in ROM 28.

As above, if the Formula 1, Formula 2 and Formula 5 are stored in advance in ROM 28 and, by image-taking by the camera 2 the reference plate and the leaves of the rice crop within the certain range in the field, and transmitting the image signal to the data processing means 20, the nitrogen content rate can be calculated based on the first crop related formula (Formula 5) at the data processing means 20. In this way, the nitrogen content rate in the rice crop within the certain range in the field or the nitrogen content rate (first crop information) in each division, i.e., No. ①–⑨ can be obtained. The values given in each division in FIG. 4 are examples of the nitrogen content rates obtained as above.

Figure 5:
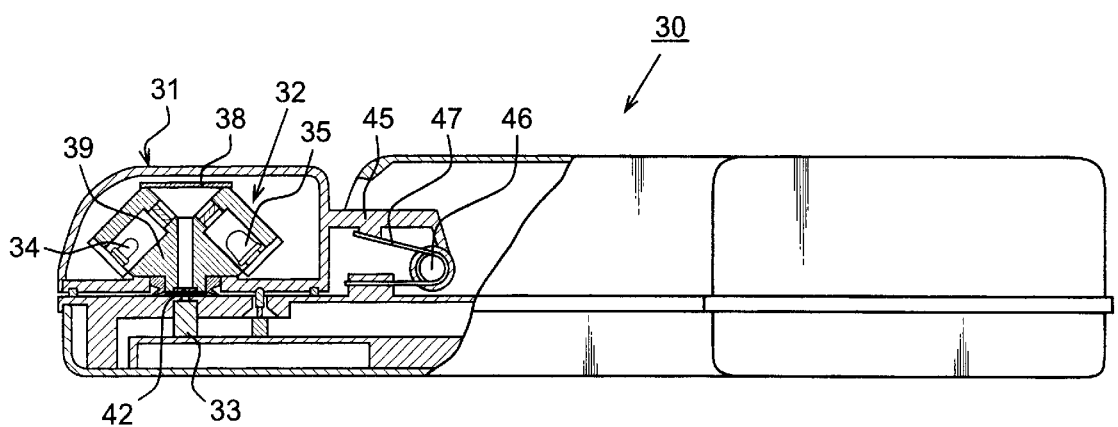
FIG. 5 is a diagram showing a coordinate of an image element and an image taken area by an image sensor.
Figure 6:
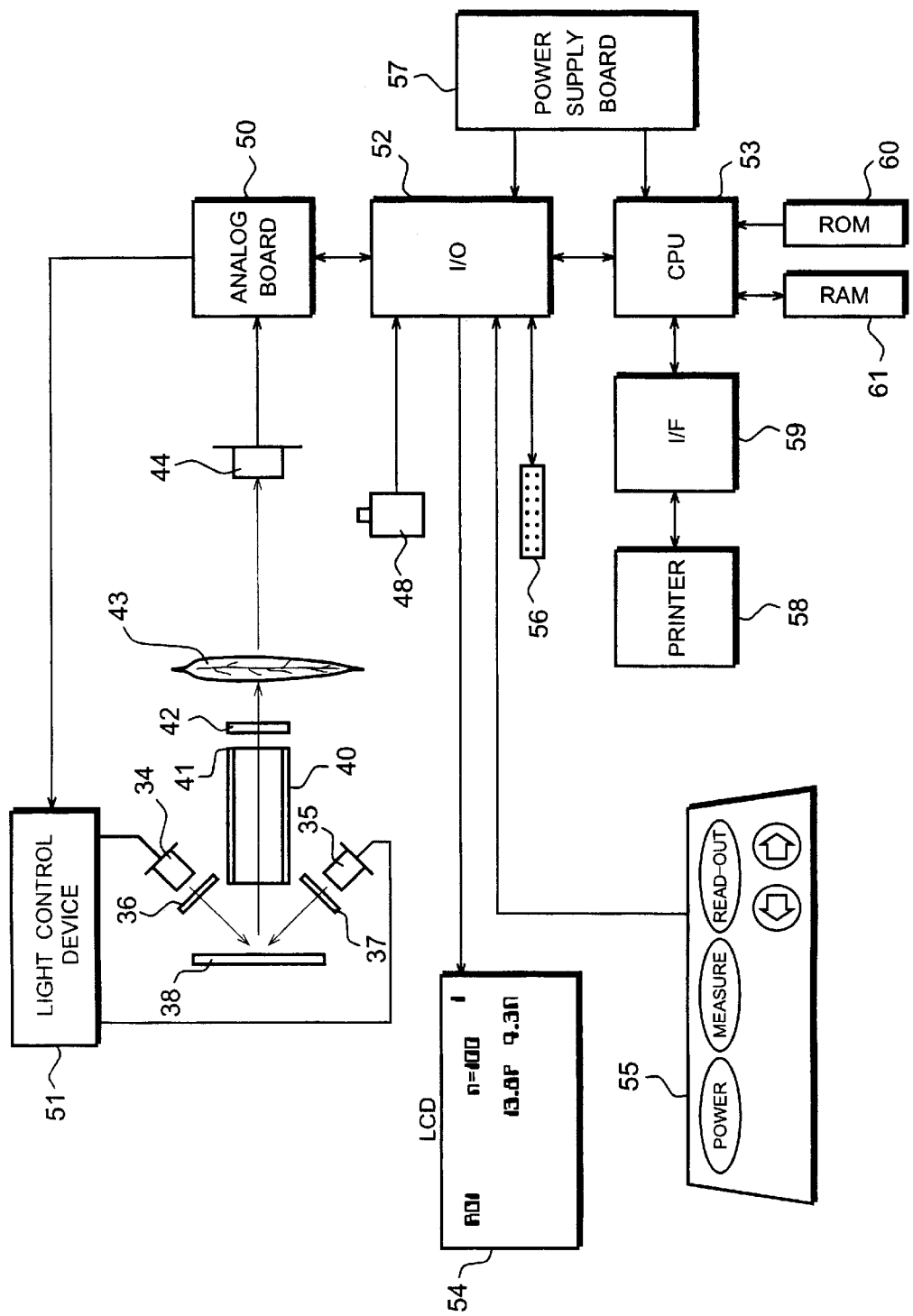
FIG. 6 is a control block diagram of the leaf blade nitrogen content measuring means.
Figure 7:
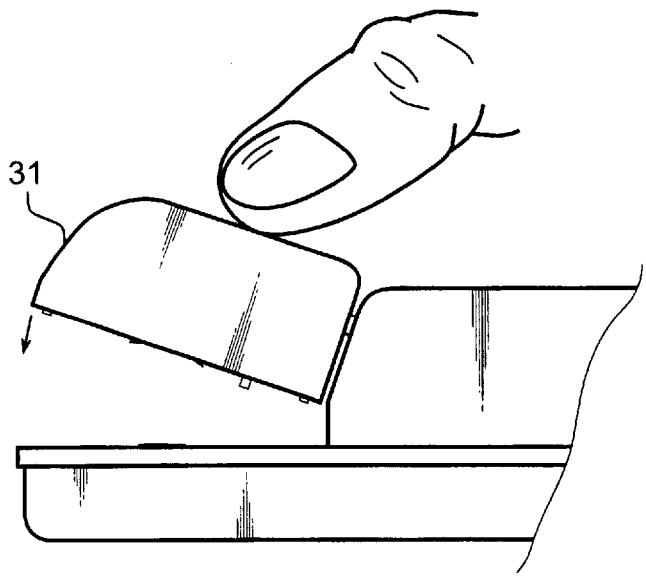
FIG. 7 is a diagram showing operation of the leaf blade nitrogen content measuring means.

Next, an example of the leaf blade nitrogen content measuring device 30 is explained with reference to FIG. 5 to FIG. 7. There the main portion of a portable type nitrogen content measuring device (hereinafter referred to as "measuring device") 30 is shown in a partly broken sectional view. The device shown in FIG. 5 and FIG. 6 is constructed such that, within the body 31, there are provided a light source section 32 and, at a lower part, photodiodes (not shown) which constitute a light amount detection device 33. As the light source 32, LEDs 34, 35, i.e., a plurality of light emitting elements having different nominal wavelength peaks on the same periphery are provided, and narrow band-pass filters 36, 37 respectively having different wavelength bands are provided to the LEDs 34, 35. As the wavelength bands, 500 nm–1100 nm are preferred and, from these wavelength bands, the narrow band-pass filters 36, 37 having relation to the leaf blade nitrogen content obtained from these wavelength bands or an arbitrary specific wavelength having relation to the color values of leaves are selected. The light emitted from each of the LEDs 34, 35 becomes the light having the specific wavelengths by the narrow band-pass filters 36, 37, and is incident on a diffusion reflection plate 38 at which the light is reflected. Further, a block 39 is formed so that the light from each of the LEDs 34, 35 is incident on the diffusion reflection plate 38 in substantially the fixed angle.

The light reflected at the diffusion reflection plate 38 is incident in a reflection light path 40 provided in the center of the block 39, and then is incident on a diffusion transmission plate 42 provided on a radiating side 41 of the reflection light path 40. The diffusion reflection plate 42 is provided perpendicular to the optical axis of the reflection light path 40, and is formed of frosted glass or milky white glass. Through the space surrounded by the reflection light path 40 and the diffusion reflection plate 38, the light passes out of the reflection light path 40 while repeating the reflection and the diffusion, and is incident in the light amount detection device 44 through the diffusion transmission plate 42 and via the leaf 43 being measured.

Further, on the top periphery of the light amount detection device 32, a top cover 31 is surroundingly provided, and the arm 45 extending from the top cover 31 is pivotally supported by the axis 46. Also, the axis 46 pivotally supporting the top cover 31 carries a coil spring 47 for the top cover 31 to be constantly urged upwardly. That is, as will be understood from FIG. 7, in conducting the measurement, the leaf 43 may be inserted into the measuring section, and the pressing down of the top portion of the top cover 31 enables the measuring operation. The timing at which the measuring is made is when, by the pressing down of the top cover 31, the pressing-down projection (not shown) presses a micro-switch 48 provided at the opposite position thereof, and the measuring (light irradiation and light amount measurement) is performed by detecting the pressing-down of the top cover 31.

Next, a light absorbency measuring device 1 shown in a block diagram in FIG. 6 is explained. The transmission light amount of the sample leaf 43 detected at the measuring section constituted by the light source section 32 and the light amount detection device 33 is converted to analog signals by the light amount detection device 44. The light source section 32 is provided with the light emitting means 51 of LEDs 34, 35. At the analog board 50, either the A/D conversion from analog to digital signals, or the V/F conversion from voltage to frequency is performed. The signals converted are inputted through the I/O board into the CPU board 53 which serves as an arithmetic and control means. In the I/O board 52, there are provided a liquid crystal display device LCD 54 for displaying the results of the calculation or operational instructions, an input section 55 for carrying out operation, a connecting port 56 of RS232C for inputting or outputting data from and to the external means, and a switch 48. To these CPU board 53 and I/O board 52, the power supply board 57 is connected for the power to be supplied. Also, the printer 58 is connected to the CPU board 53 via a printer I/F board 59. Further, to the CPU board 53, a read-only memory (hereinafter referred to as "ROM") 60 and a read and write memory (hereinafter referred to as "RAM") 61 are connected. In the ROM 60 are stored a plurality of calibration curves on a field to field basis or a kind (breed) to kind basis. The calibration curves constitute a relation formula (second crop related formula) for obtaining a nitrogen content rate (second crop information), wherein absorbency is calculated from a plurality of the received amounts of the light obtained by irradiating the light on a plurality of leaves for which the nitrogen content rates are measured in advance, and the multiple regression analysis is conducted by using the absorbency as explanatory variables and a plurality of known nitrogen content rates as objective variables. As to the multiple regression analysis, the procedures with which the above Formula 5 is obtained have already been explained so that no explanation is repeated here. Further, the ROM 60 stores a series of programs, which execute operations from the measuring and calculation of the absorbency to the displaying of the calculation results, for measuring the absorbency at the measuring device 30 and calculating the quality such as the nitrogen content rates.

The function of the measuring device 30 constructed as above is explained hereinafter. When, after a sample leaf 43 is inserted in the measuring device 30, the top cover 31 is pressed down, the signal from the switch 48 is transmitted to the CPU board 53. From the CPU board 53, a signal is outputted to the light emission control means 51, and the light emission signal is transmitted from the light emission control means 51 to the light source section 32. In this way, the light is irradiated on the sample leaf 43 alternately from the LED 34 and the LED 35. The light emitted from the LEDs 34, 35 turns, through the narrow band-pass filters 36, 37, to the light of specific wavelengths, that is, the light of near infrared ray region and visible ray region. Since the light reaches the light amount detection device 44 from the diffusion transmission plate 42 while repeating reflection and diffusion as already explained, the light is irradiated on the sample leaf 43 in the same degree of uniformity as in an integrating sphere.

When the light is irradiated on the sample leaf 43, its reflection light or transmission light is received by the light amount detection means 44 separately for each of the LEDs 34, 35, and the received light signal is communicated to the analog board 50 for A/D conversion. The A/D conversion is made at the analog board 50 and the signal converted is inputted into the CPU board 53 via the I/O board 52. At the CPU board 53, from the transmission light or the reflection light of the sample leaf 43, the reflectivity, transmissivity, or absorbency is calculated, and the values thus calculated are stored in RAM 61. Based on the absorbency stored in RAM 61 and the relation formula for obtaining the nitrogen content rate stored in advance in ROM 33, it is possible to calculate the nitrogen content rate of the measured leaf. The input section 55 is provided with a power source switch 55a for switching the measuring device 30, a measuring switch 55 enabling to measure the transmission light, and a reading-out switch 55c equipped with function of reading-out switching of a calibration curve (formula) stored in ROM 60, or absorbency or transmission light data or calculation results stored in RAM 61, or sample numbers.

Hereunder, a first embodiment of the invention dealing with a diagnosis of crop in the fields based on the first crop information and the second crop information is explained. By the camera 2, the measurement is made of reflection light from the reference plate 3 and of, for example, an amount of reflection light of a wavelength having relation to the nitrogen content rate, which is crop information subject to increase and decrease depending on the growth of rice plant from the field 1 under exposure to natural light. As shown in FIG. 3 and FIG. 4, in the data processing unit 20, the reflectivity is calculated based on the amount of reflection light of leaves within the light receiving range measured by the camera 2 and on Formula 2 for obtaining the reflectivity within the light receiving range stored in ROM 28 and, by the reflectivity thus obtained and the first crop related formula stored in ROM 28, the nitrogen content rate within the light receiving range of the camera 2 which is the first crop information, and the nitrogen content rate is stored in RAM 29.

Next, explanation is made in respect of a case where the nitrogen content rate of the leaves of the rice plant growing within the light receiving range of the camera 2. The nitrogen content rate (a second crop information) of the leaves of the rice plant measured by the device 30 is a measured value obtained directly from the leaves of the rice plant, and this value is one which has not been influenced by such factors as a measurement direction and a planting density. Therefore, according to the present invention, a difference between the first crop information and the second crop information is calculated. For example, assuming that the first crop information measured first is 4.0% and the second crop information measured by the device 30 is 3.0%, the value by the device 30 is made the second crop information and stored in RAM 61. The second crop information obtained by the measurement device 30 is forwarded to the data processing unit 20 from the connecting port 56 of the measurement device 30 via the I/F board of the data processing unit 20, and this information is stored in RAM 29. At the unit 20, based on this difference of −1% between the first crop information and the second crop information in RAM 29, the first crop information is compensated to 3.0% by adding −1% to the first crop information.

That is, the difference is newly stored in RAM 29 as a compensating value, and the difference of −1% is added to compensate all the values calculated by unit 20 after the measurement by the camera 2 of the reflection light of other crop leaves within the light receiving range. In this way, the measurement not influenced by the measurement direction and the planting density is realized by the camera 2 and the unit 20. Moreover, after the storing of the compensating value in RAM 29, the measurements for a number of times by the device 30 are rendered unnecessary at least for the same field, and only one time measurement by the camera 2 results in such a high precision measurement which has not been the case ever before. Further, the measurement of nitrogen content rate by the measurement device 30 is not necessary to be conducted with respect to all the crop leaves within the field, but it is sufficient to measure the same with respect to a representative crop leaf within the field 1.

Next, a second embodiment of the invention for nutrition diagnosis is hereinafter explained. By the camera 2, the measurement is made of reflection light from the reference plate 3 and of, for example, an amount of reflection light of a wavelength having relation to the nitrogen content rate, which is crop information subject to increase and decrease depending on the growth of rice plant from the field 1 under exposure to natural light. As shown in FIG. 3 and FIG. 4, in the data processing unit 20, the reflectivity is calculated based on the amount of reflection light in divided sections No. ① through No. ⑨ measured by the camera 2 and on the Formula 2 for obtaining the reflectivity for each section stored in ROM 28 and, by the reflectivity thus obtained and the first crop related formula stored in ROM 28, the nitrogen content rate on a section to section basis which is the first crop information, and the nitrogen content rate is stored in RAM 29.

By the operator or by the unit 20, the nitrogen content rates of arbitrary two sections out of the rates obtained here on a section to section basis are selected, preferably the selected sections being ones in which the value of nitrogen content rate is maximum and the value of nitrogen content rate is minimum. In the sections selected as in FIG. 4, the measurement is made by the measurement device 30 for the nitrogen content rate of leaves of the rice crop growing in the sections of the field corresponding, for example, to the section No. ⑤ in which the value as being 4.2% is maximum and to the section No. ⑦ in which the value as being 2.4% is minimum. The nitrogen content rates measured here are ones derived without receiving any influence from the measuring direction or from the planting density.

In the measurement device 30, from the amount of received light obtained directly from the leaf blade of the rice crop corresponding to the two sections selected in the field described above by irradiating the light of the wavelength having relation to the leaf blade nitrogen content rate which is crop information subject to increase or decrease depending on the growth of the crop, the nitrogen content rate relating to the above two sections is calculated based on the absorbency which, in this embodiment, is converted from the amount of the received light, and the second crop related formula predetermined for obtaining the leaf blade nitrogen content rate from the absorbency. Then, the nitrogen content rates of 3.0% for No. ⑤ section and of 2.4% for No. ⑦ section are obtained, and these values are stored in RAM 61 as the second crop information. Each of the nitrogen content rates for the two sections obtained by the measurement device 30 is forwarded to the data processing unit 20 from the connecting port 56 of the measurement device 30 via the I/F board of the data processing unit 20, and this information is stored in RAM 29.

Figure 8:
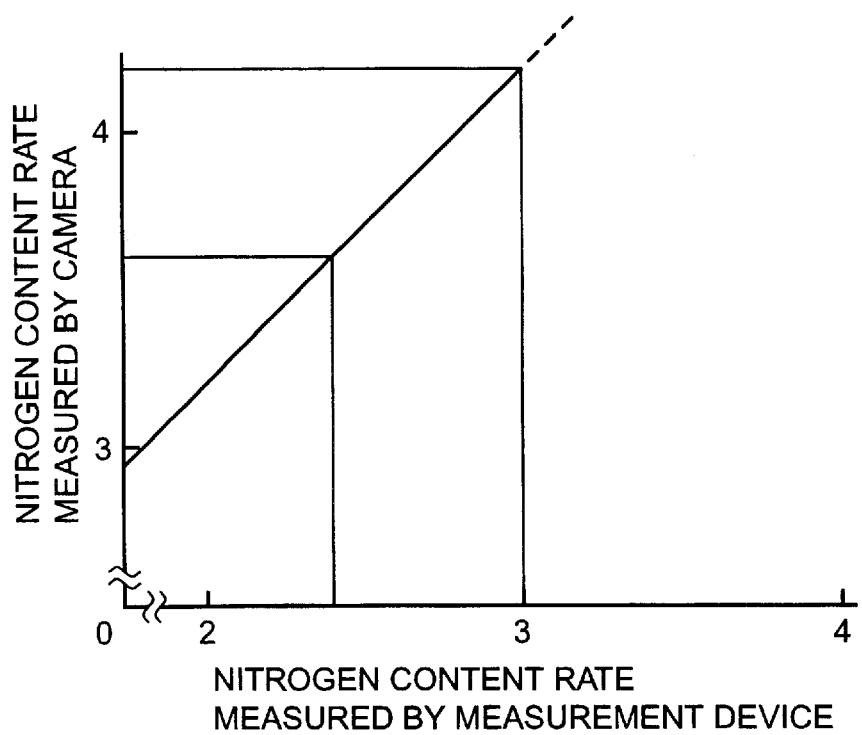
FIG. 8 is a graph showing relation of nitrogen contents between the measuring by the leaf blade nitrogen content measuring means and the image-taking by camera.
Figures 9, 10:
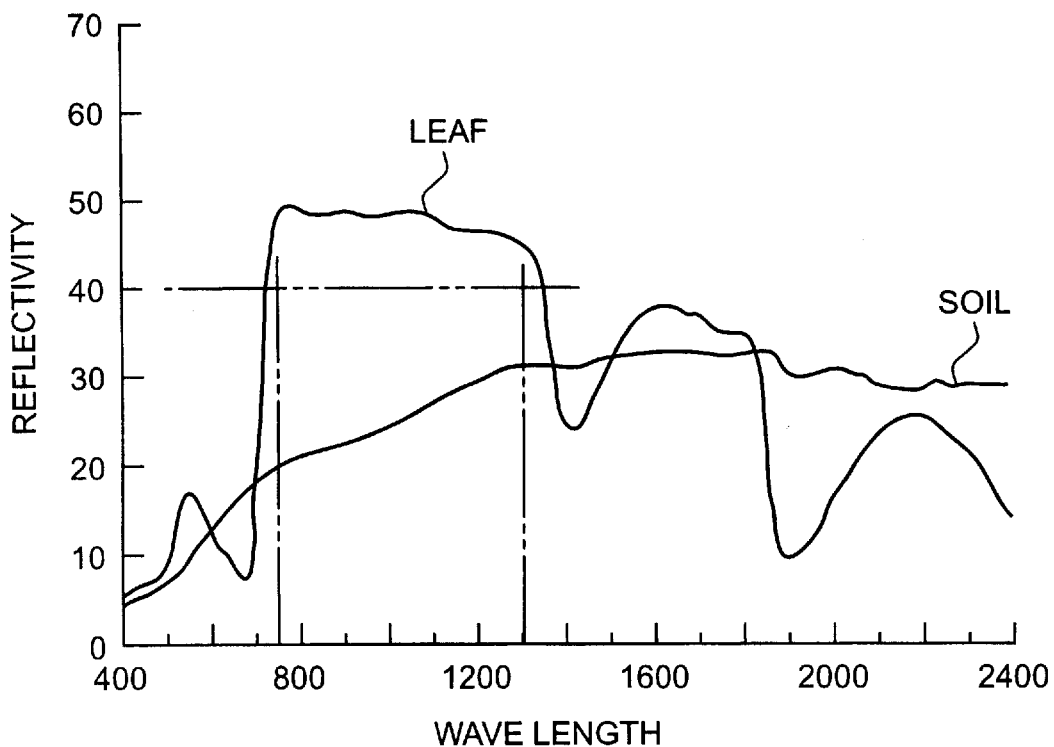
FIG. 9 is a table showing, in a plurality of divisions, values by compensation for nutritious diagnosis.
FIG. 10 is a graph showing reflectivity curves with respect to wavelengths of crop leaves and soil.

With reference to FIG. 8, explanation is made on the third crop information which is obtained, based on the nitrogen content rates for the two sections constituting the second crop information stored in RAM 29, by compensating the first crop information stored also in RAM 29 for each of the sections (nitrogen content rates in sections No. ①–No. ⑨). FIG. 8 is a graph in which the nitrogen content rate (the second crop information) measured by the measurement device 30 is shown in the axis of abscissa while the nitrogen content rate (the first crop information) calculated by the data processing unit 20 is shown in the axis of ordinate. That is, the graph represents the nitrogen content rates of 3.0% and 2.4% for two sections measured by the measurement device 30, and the nitrogen content rates of 4.2% for No. ⑤ section and of 3.6% for No. ⑦ section calculated by the data processing unit 20. In this way, by the nitrogen content rates for two sections measured actually and directly from the leaf blades of the rice crop by the measurement device 30 and the straight line represented by the simple function constituted by the relationship with the nitrogen content rates measured by the camera 2, the interrelation is made clear, and by this simple function, the nitrogen content rates measured by the camera 2 are compensated. Here, the compensation is made by the straight line represented by the function, and this function is stored in RAM 29 as a compensation conversion formula. In FIG. 8, specifically, the nitrogen content rate of 4.2% for No. ⑤ section is compensated to 3.0%, and the nitrogen content rate of 3.6% for No. ⑦ section is compensated to 2.4%. Similarly, as shown in FIG. 9, the values for other remaining sections are compensated based on the compensation conversion formula determined by the interrelation of the two sections. This is how the third crop information is obtained. The third crop information thus obtained is for the nine sections but, by obtaining from these a further average value, it is possible to treat it as a single crop information for the range for which the image was taken by the camera. As for the compensation coefficient, the value represented by the simple function using the representative value of the two sections has been shown and explained, but this compensation coefficient may well be an interrelation coefficient obtained by using the crop information of the overall sections image-taken by the camera as an explanatory variable and the crop information of the overall sections obtained by the measurement device 30 as an objective variable, and such coefficient can be utilized whether linearly or non-linearly.

Subsequently the nitrogen content rate measured by the camera 2 is compensated based on the compensation conversion formula as in FIG. 8 by the data processing unit 20 so that the resulting value can be used as a value enhancing a more precise measurement. Therefore, as compared with the conventional method in which, only by the measurement device 30, the nitrogen content rate is measured of the leaf blades at a plurality of points in the field, it is possible to obtain faster the information being sought. Further, when taken into account the fact that the obtaining of the nitrogen content rate of the crop by image-taking of the reference plate and the field is still under a researching stage, it must be considered that the method described above will greatly contribute to the enhancement of the precision in the measurement. The measurement of the nitrogen content rate by the measurement device 30 is not conducted for all the leaves of the crop in the field 1, but may be conducted only for some representative leaves in the field 1.

It is obvious that the crop information to be obtained from the field 1 according to the first and second embodiments of the invention for nutritious diagnosis defers depending on the position of the camera 2 with respect to the object. That is, the field 1 here may be one field divided by a commonly called "furrow" or may be larger than the one field in area. What is important in defining the compensation value or the compensation coefficient is that the source of the crop information obtained by the camera and the source of the crop information obtained by the measurement device 30 are from the same field. As to the section in the second embodiment of the invention for the nutritious diagnosis, it does not matter whether the crop information obtained from the one field for which the image is taken by one image-taking action is divided into a plurality of sections, or the crop information obtained from a field smaller than the one field is divided into a plurality of sections. However, it is important that, in defining the compensation value or the compensation coefficient, the crop information collected is based on the same source.

Next, a third embodiment of the invention for diagnosis is hereinafter explained. Here, as a method for obtaining the information for a plurality of sections divided from the field 1, the amount of reflection light is obtained by the camera 2 by the same number of image-taking actions as the number of the plurality of sections. That is, the difference from the second embodiment for diagnosis is that the crop information is obtained by the camera 2 individually for respective sections. In this way, since the amount of the crop information obtained on a section to section basis is larger than that obtained by one time image-taking according to the second embodiment, the precision of the compensation coefficient defined by the interrelation with respect to the crop information by the measurement device 30 is enhanced. Since the way how to determine the compensation coefficient is the same as in the second embodiment, no explanation is made here. The compensation coefficient here may be interrelation coefficient obtained by making the crop information of all sections image-taken by the camera as an explanatory variable and the crop information of all sections obtained by the measurement device 30 as an objective variable. The fact that such coefficient can be utilized whether linearly or non-linearly is the same as in the second embodiment.

Subsequently the nitrogen content rate measured by the camera 2 is all compensated based on the compensation conversion concept shown in FIG. 8 by the data processing unit 20 so that the resulting value can be used as a value which enhances a more precise measurement. Therefore, as compared with the conventional method in which, only by the measurement device 30, the nitrogen content rate is measured of the leaf blades from a plurality of points in the field, it is possible to obtain extremely faster the information being sought. Further, when taken into account the fact that the obtaining of the nitrogen content rate of the crop by image-taking of the reference plate and the field is still under a researching stage, it must be considered that the method described above will greatly contribute to the enhancement of the precision in the measurement. The measurement of the nitrogen content rate by the measurement device 30 is not conducted for all the leaves of the crop in the field 1, but may be conducted only for some representative leaves in the field 1.

It is obvious that the crop information to be obtained from the field 1 according to the third embodiment of the invention for nutritious diagnosis defers depending on the position of the camera 2 with respect to the object. That is, the field 1 here may be one field divided by what is commonly called "furrow" or may be larger than the one field in area. What is important in defining the compensation value or the compensation coefficient is that the source of the crop information obtained by the camera and the source of the crop information obtained by the measurement device 30 are from the same field and the same section. Further, as to the section in the embodiment of the invention, it does not matter whether the crop information obtained from the one field image-taken by one image-taking action is taken as the one section, or the crop information obtained from a field smaller than the one field is taken as the one section. However, it is important that, in defining the compensation value or the compensation coefficient, the crop information collected is based on the same source.

As the foregoing, the measurement by the camera enables the compensation of the errors caused by weather by using the reference plate 3 and the errors caused by the measuring direction and the planting density may be compensated by using the values obtained by the measuring device 30. That is, when the compensation is made by the measuring device 30, since, in the measurement by the camera 2, the compensation value compensating the weather errors by the reference plate caused by weather is compensated by the value obtained by directly measuring the crop leaves measured by the same camera 2 and, since the value with which the crop leaves are directly measured by the values of the measuring device 30 is a value obtained irrespective of the measuring direction and the planting density, the value finally obtained by the compensation is a value not having been influenced by various external factors unlike in the so-called remote sensing where only a conventional camera 2 and data processing are used.

In collecting the crop information by the camera 2 in the first to third embodiments, the information obtained by the camera 2 is not necessarily all crop information. That is, when the data in each of the image elements is examined, it is found that, while almost all are crop information, it is possible that, depending on the planting density, the soil is included in the image, since the crop information is obtained in the state in which the crop is being looked down. Thus, according to the invention, the image elements received as the crop information and the image elements received as other than the crop information are separated, and only the data of the image elements received as the crop information is taken as the crop information.

Figure 11A:
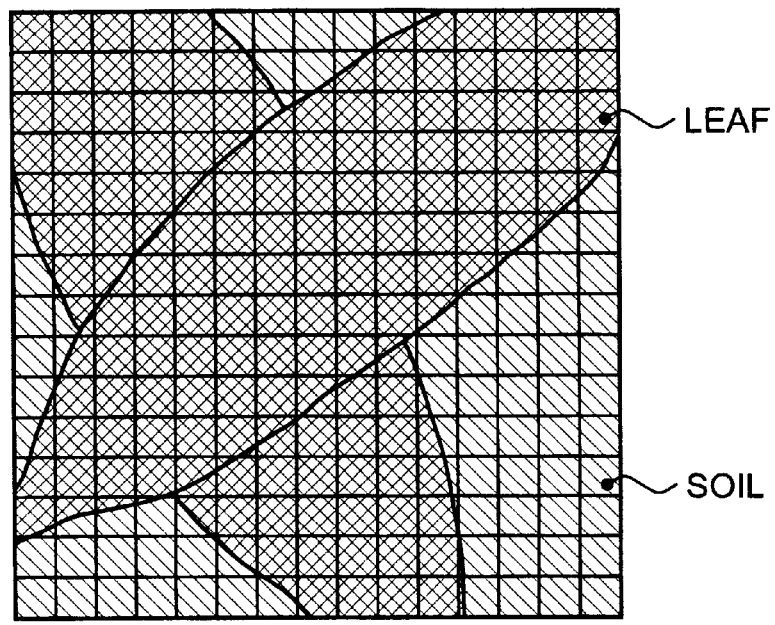
FIG. 11 is a figure showing the data of the light received from the crop leaves and the soil obtained by the camera.
Figure 11B:
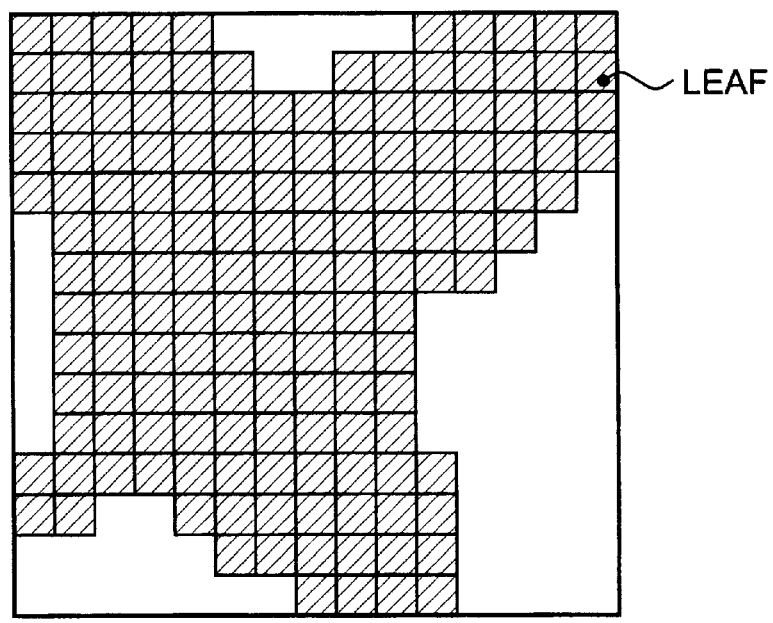

FIG. 10 is a graph showing changes with respect to the wavelengths in reflectivity of the soil and in reflectivity of the crop leaf. In the wavelengths of 750 nm–1300 nm, it has been found that the difference in the order of 20% occurs in the reflectivity of the crop leaf with respect to the reflectivity of the soil. Thus, the reflectivity obtained by Formula 1 and Formula 2 showing, for example, a value exceeding 40%, is treated as the data of the light received from the crop leaf. On the other hand, a value below the above percentage is treated as not being the data of the light received from the crop leaf and is cancelled. Only the data of the light received exceeding 40% is utilized as it is, or utilized after obtaining an average value for each image element, and the value is treated as being the crop information obtained by the camera 2. For example, FIG. 11(a) assumes that the data of the light received are in a plurality of image elements. In this case, for a unit of 1 pixel, a portion represented by slanted grids is reflection light from the crop leaf and its reflectivity is above 40%. If the portion of the slanted grids is for the soil other than the crop leaf and, if the calculation shows that the reflectivity is below 40%, the data of the received light of the image element whose reflectivity is below 40% is cancelled, and the data useful as the crop information is the data of the received light obtained from the image elements shown by slanted stripes as shown in FIG. 11(b). In this way, according to the present invention, the selection of the data of the received light by the camera 2 has been added to the determination of the compensation value or compensation coefficient based on the crop information through the camera 2 and the crop information through the measuring device 30. Thus, the information selectively obtained by the camera 2 is information obtained only from the crop leaves. The information obtained from the measuring device 30 is, of course, information directly measured from the crop leaves so that the diagnosis of the crop made by the crop information and the compensation value or the compensation coefficient is accurate and precise.

Figure 12:
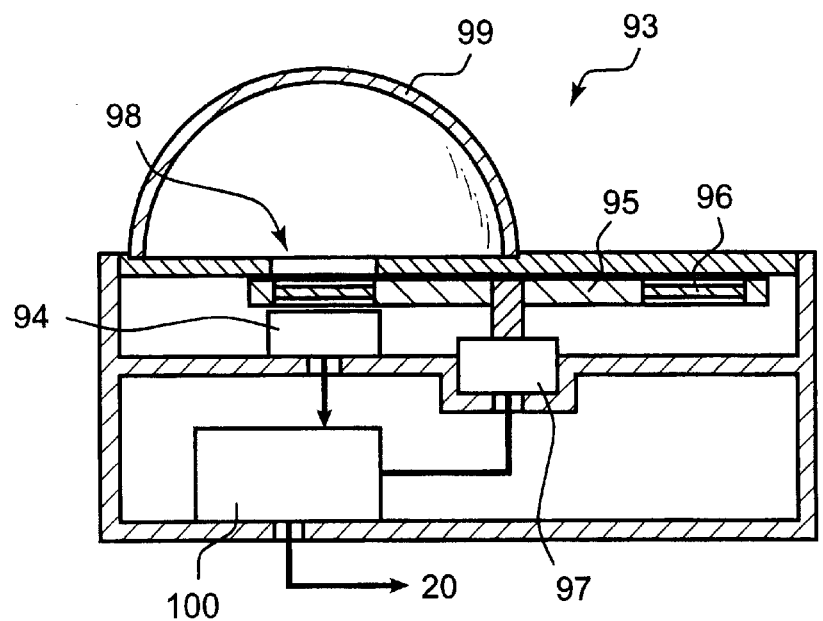
FIG. 12 is a side sectional view diagrammatically showing an illuminometer for measuring incident light.

It has been explained heretofore that the measuring of the reflection light of the crop leaves by the camera 2 is obtained by measuring the reflection light of the reference plate, but it is possible to measure the incident light in the form of the measurement by an illuminometer. FIG. 12 diagrammatically shows the illuminometer 93. This illuminometer is equipped with a photoelectric conversion section (silicon sensor) 94 having spectrum characteristics from near infrared ray regions to visible ray regions, and a plurality of narrow band-pass filters 96 for selecting the light incident to the photoelectric conversion section 94 are provided to the peripheral portion of the filter wheel 95 which is rotated by the stepping motor 97. By rotating this filter wheel 95, the plurality of filters 96 are switched. At the light receiving surface side (upper portion in FIG. 12) of the photoelectric conversion section 94, there is provided an opening section 98 in a shielding plate and, above this, there is provided a diffusion dome 99 formed by a diffusion reflection plate with the photoelectric conversion section 94 being in the center. The photoelectric conversion section 94 and the stepping motor 97 are communicated to a control section 100 which rotates the stepping motor 97 for switching the filters 96 and outputs signals of the photoelectric conversion section 94. As to the kinds of the filters 96, they are the same as those of the filters 5 of the camera 2. The control section 100 is connected to and controlled by an I/O port 25 (FIG. 3) of the data processing means 20. The filters 96 include a filter which interrupts the light and, in this way, zero compensation is enabled by the switching of the filters 96.

By the signal from the data processing means 20, the control section 100 of the illuminometer 93 switches the filter 96 to the intended filter. At this time, the amount of the natural light which diffusion-reflects and enters from the diffusion dome 99 is detected through the filter 96, and the signal detected by the photoelectric conversion section 94 is transmitted to the data processing means 20. At the data processing means 20, the amount of light obtained by the illuminometer 93 is made the incident light amount Y and is applied to Formula 2, so that the reflection light amount obtained from the crop leaves can be calculated into the reflectivity. When the illuminometer 93 is used, the first crop related formula can be obtained based on the reflectivity of the time when the illuminometer 93 is made the reflection light amount.

The above explanation has been made on the premise that the camera 2 image-takes a part (1 m$^2$) of one crop field. However, it is possible for the one entire field to be image-taken with the compensation being made similarly, and it is possible to make the measurement at each special time period such as a panicle initiation stage which is the growth period of the rice crop, or it is possible to make compensation for a part of the field and estimate the nitrogen content for the entire field. In this method, the compensation may be more effective if it is conducted on a kind to kind basis, or a district to district basis (or a field to field basis). That is, if ROM 28 stores a plurality of compensation calibration curves separately for individual kinds or individual districts, they may be read out and used every time the need arises. The camera used in the embodiments has resolution of 240,000 pixels. If the field of 10 ares is to be image-taken at a time for obtaining the crop information, the image elements are 250 pixels per one square meter. If the resolution in this order is available, the necessary image can be taken with the usage of a satellite instead of the case wherein the camera 2 is placed on the ground. Further, the camera for image-taking may be installed in a balloon, a radio-controlled plane or a piloted plane.

For the nitrogen content rate in the field as discussed above, it has been conventionally researched for the rice crop on a kind to kind basis or a district to district basis as to the best nitrogen content rate at arbitrary growth periods such as a panicle initiation stage and a reduction division stage. It is possible to compare the nitrogen content rate by the compensated first crop information or third crop information obtained according to the invention and the nitrogen content rate which the conventional research has determined as being reference along with the growth of the crop. When the comparison is made against such reference, whether the nitrogen content rate is above or below becomes clear, and it is possible to decide accordingly the amount of the subsequent fertilization. What has been described above is applicable to the color values of the leaves. Since, between the color values and the nitrogen content rates in the leaf blades, there are very high interrelations, and changes in the both are similar to each other. Thus, the explanations and discussions made in the foregoing may be considered applicable to any embodiments relating to the color values of the leaves. The methods explained with reference to FIG. 1 to FIG. 3 are applicable to other than the nitrogen content rate and the color values, such as height of a plant, a dry plant weight, and nitrogen absorbent amount, and are also applicable to plant other than the rice crop.

Figure 13:
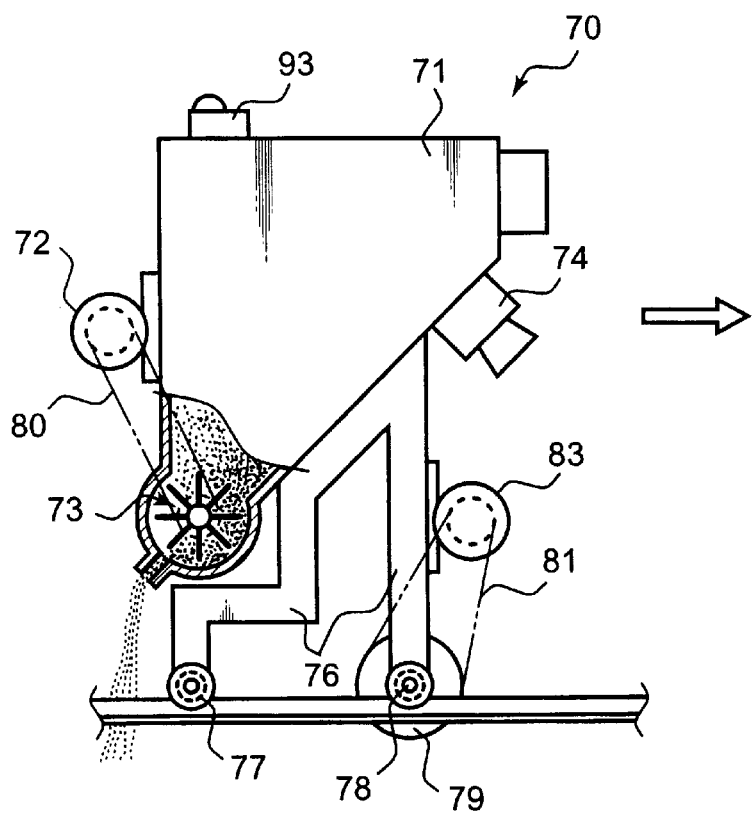
FIG. 13 is a side view showing an automatic fertilizer distributor.
Figure 14:
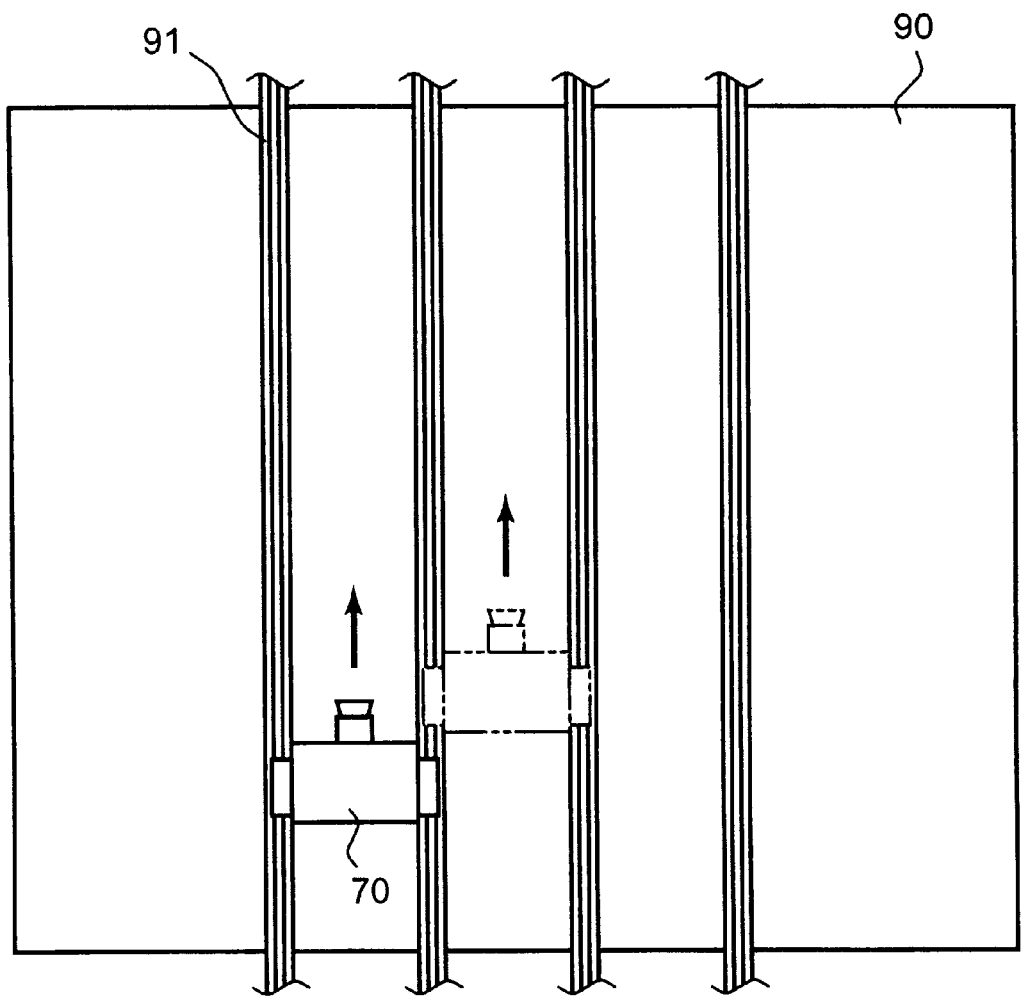
FIG. 14 is a plan view of the crop field when the automatic fertilizer distributor is utilized in the crop field.

Now, explanation is made for the application of the above described methods to an automatic fertilizer distributor. FIG. 13 shows the automatic fertilizer distributor 70 equipped with a fertilizer tank 71 and a screw 73 which is provided under the tank 71 and rotated by a motor 72. At the side of the tank 71, there are provided a camera 74 for measuring nitrogen content from leaves of a plant in a crop field, and an illuminometer 93 for measuring incident light. A leg portion 76 for supporting the tank is provided with a roller means 77 which allows the tank to run thereon. A rotary axis 78 of the roller means 77 carries a pulley 79 which receives the driving force of the motor 83. The motor 72 and the screw 73 carry a belt 80, and the motor 83 and the pulley 79 carry a belt 81. The camera 74 and the motor 72 are connected to a control means 82. As their power sources, use may be made of storage battery or of AC power supply connected by a cable. FIG. 14 is a plan view of the crop field 90 in which the rails 91 are provided to allow the automatic fertilizer distributor 70 to run thereon. By allowing the roller means to run on rails 91, it is made possible for the automatic fertilizer distributor to carry out the fertilization in the crop field 90.

The fertilizer distributor as constructed above is explained with reference to the data processing device 30 shown in FIG. 3. The control means 76 may have similar construction as that of the data processing device 30 and, stored in the ROM 28, are above explained Formula 1 and Formula 2 which are necessary for calculating the reflectivity for obtaining the first crop information, the first crop related formula (Formula 5), a compensation conversion formula (FIG. 8) determined by correlation of two divisions for obtaining the third crop information, and a calculation formula for calculating the amount of fertilizer based on differences between the reference nitrogen content rates on a breed (kind) to breed basis at a specific stage (fertilizing stage) of the growth and the nitrogen content rates.

On starting the operation, the motor 83 drives the pulley 79 to rotate, and the automatic fertilizer distributor 70 starts running along the rails 91 in a constant speed. As the running starts, the data processing device 30 receives the incident light from the illuminometer 93. Further, the camera 74 picks up the image of the crop field which is information of field of view. When the reflection light of the crop field 90 and the incident light are obtained as above, the reflectivity of the plant in the crop field is calculated from the incident light of the illuminometer 93, the formula 2 in the ROM 28, and the reflection light of the crop field. As the reflectivity is calculated, the nitrogen content rate which is the first crop information is calculated from the first crop related formula in the ROM 28. When the nitrogen content rate is calculated as the first crop information, the third crop information is obtained based on the calculated value and the compensation conversion formula in the ROM 28. The nitrogen content rate as the third crop information obtained as above has almost the same degree of precision at that obtained by other embodiments of the invention.

The nitrogen content as obtained above is compared with the known nitrogen curve (reference values) at the specific stage during the growth stored in the ROM 28 and, by comparing the nitrogen content rate at the present crop field with the nitrogen content of the reference, any differences between them are calculated. The comparison here is made such that, if the specific stage during the growth at which the present measurement has taken place is, for example, a panicle initiation stage, the reference value to be compared with follows that of the same panicle initiation stage. Thus, it is necessary that the time or stage of measurement be inputted in the control means 82 in advance to the measurement. In other words, the automatic fertilizer distributor 70 is used at the specific time or stage. The calculated differences with respect to the reference values are converted into the amounts of fertilizer determined in advance based on the differences and, based on such amounts of fertilizer, the rotating speed of the motor 72 is determined and the motor 72 is driven. Naturally, with an increase in the rotating speed of the motor 72, an application rate of the fertilizer increases and, on the other hand, with a decrease in the rotating speed, an application of the fertilizer decreases. Further, even where no differences occur, the application of fertilizer may well be effected for the possible fertilization for the future.

Figure 15:
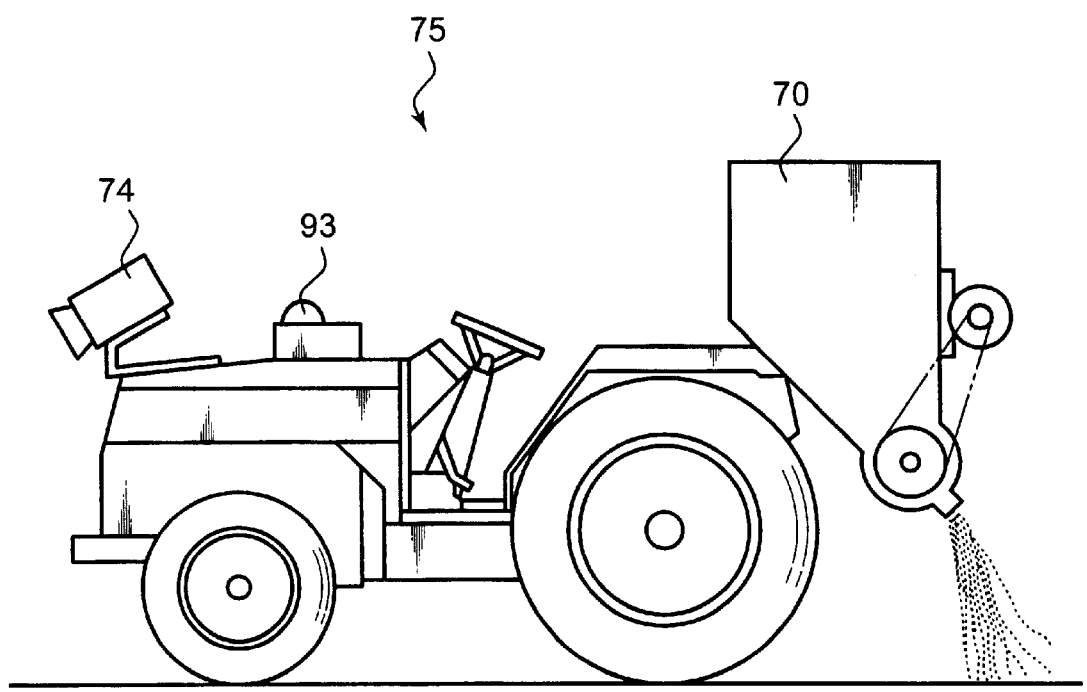
FIG. 15 is a side view of a cultivator in which the device according to the invention is installed.

The foregoing has explained that the automatic fertilizer distributor 70 runs on the rails 91 set on the crop field 90. However, as shown in FIG. 15, it is possible to attach the automatic fertilizer distributor 70, the camera 74 and the illuminometer 93 to a front end of a conventional cultivator 75. In this way, even when the crop field does not have a regular shape (not square), the fertilization may be completed according to the crop information as of immediately before the running of the fertilizer distributor 70. Even today, the amount of fertilizer to be applied is empirically determined by comparing the color of plant leaves or the measured values of leaf blade nitrogen content with the reference values of these at the growth stage gained by experience and, even after the fertilization has been mechanized, it has been normal to apply average fertilization to the entire crop field. However, when the features of the present invention are applied, the amounts of fertilizer are automatically calculated and, moreover, it is possible to apply fertilizer proportionally to a portion concerned in the crop field.

The nutritious diagnosis of the crop can be made in a simple and easy way of calculating the nitrogen content of the crop by measuring the reflection light of crop leaves, and in addition the nutritious diagnosis of the crop can be made precisely and accurately by calculating the nitrogen content rate of the crop by directly irradiating the crop leaves and measuring the reflection light or the transmission light.

Also, in the simple and easy nutritious diagnosing method of the crop by measuring the reflection light from the crop leaves and calculating the nitrogen content in the crop, any errors caused by the measuring direction, quivering of leaves in wind, difference in planting density can be compensated by excellent precision with which the measuring of the reflection light or the transmission light by directly irradiating the crop leaves is made, and the diagnosing the crop by calculating the nitrogen content of the crop is made. By the simply and easy method of diagnosing the crop, it is made possible to carry out the diagnosis with a higher precision than that obtained by the conventional methods.

While the invention has been described in its preferred embodiments, it is to be understood that the words which have been used are words of description rather than limitation and that changes within the purview of the appended claims may be made without departing from the true scope of the invention as defined by the claims.

What is claimed is:

1. A method of diagnosing nutritious condition of crop in a fixed area in a plant field under exposure to natural light, said method comprising the steps of:
    measuring reflectivity of light which comes from a predetermined crop in said plant field and whose wavelengths have relation to crop information which increases or decreases depending on growth of crop;
    obtaining first crop information of said predetermined crop by applying said measured reflectivity to a first crop related formula established in advance for obtaining crop information from reflectivity, and storing said first crop information;
    irradiating a leaf blade of said predetermined crop, and measuring light amount of at least either one of transmitted light and reflected light whose wavelengths have relation to crop information which increases or decreases depending on growth of crop;
    obtaining second crop information of said predetermined crop by applying said measured light amount to a second crop related formula established in advance for obtaining crop information from light amount, and storing said second crop information;
    calculating a difference between said first crop information and said second crop information;
    measuring reflectivity of light from unknown crop in said same plant field, whose wavelengths of light have relation to crop information which increases or decreases depending on growth of crop;
    obtaining said first crop information of said unknown crop by applying said measured reflectivity of said unknown crop to said first crop related formula;
    correcting said first crop information of said unknown crop based on said difference; and
    determining the nutritious condition of said unknown crop in said plant field based on said corrected first crop information.

2. A method of diagnosing nutritious condition of crop in a plant field according to claim 1, further comprising a step of:
    storing said difference calculated from said first crop information and said second crop information.

3. A method of diagnosing nutritious condition of crop in a plant field according to claim 1, in which said first crop information is obtained for each unit plant field.

4. A method of diagnosing nutritious condition of crop in a plant field according to claim 1, in which said first crop information is obtained for each arbitrarily predetermined unit area of a plant field smaller than a unit plant field.

5. A method of diagnosing nutritious condition of crop in a plant field according to claim 1, in which said crop information is an amount of nitrogen content.

6. A method of diagnosing nutritious condition of crop in a plant field according to claim 2, in which said crop information is an amount of nitrogen content.

7. A method of diagnosing nutritious condition of crop in a plant field according to claim 1, in which said crop information is a leaf blade color.

8. A method of diagnosing nutritious condition of crop in a plant field according to claim 2, in which said crop information is a leaf blade color.

9. A method of diagnosing nutritious condition of crop in a plant field according to claim 1, in which, for measuring the reflectivity of light whose wave-lengths having relation to the crop information which increases or decreases depending on growth of crop, the reflection light of the crop is image taken by an image-taking means having a plurality of pixels, only the pixels having received the reflection light corresponding to the crop are selected and, based on the data of the light received of the selected pixels, said first crop information is obtained.

10. A method of diagnosing nutritious condition of crop in a plant field according to claim 2, in which, for measuring the reflectivity of light whose wave-lengths having relation to the crop information which increases or decreases depending on growth of crop, the reflection light of the crop is image taken by an image-taking means having a plurality of pixels, only the pixels having received the reflection light corresponding to the crop are selected and, based on the data of the light received of the selected pixels, said first crop information is obtained.

11. A method of diagnosing nutritious condition of crop in a fixed area in a plant field under exposure to natural light, said method comprising the steps of:
    measuring reflectivity of light which comes from a predetermined crop in said plant field and whose wavelengths have relation to crop information which increases or decreases depending on growth of crop, and obtaining reflectivity on a division-to-division basis of a plurality of divisions into which said plant field is divided;
    obtaining first crop information of said predetermined crop for each division by applying said reflectivity for each division to a first crop related formula established in advance for obtaining crop information from reflectivity, and storing said first crop information for each division;
    selecting the first crop information of at least two divisions among said plurality of divisions;
    irradiating a leaf blade of said predetermined crop in said selected two divisions, and measuring light amount of at least either one of transmitted light and reflected light whose wavelengths have relation to crop information which increases or decreases depending on growth of crop;

obtaining second crop information of said predetermined crop in said selected two divisions by applying said measured light amount for each division to a second crop related formula established in advance for obtaining crop information from light amount, and storing said second crop information for said selected two divisions;

determining a compensation conversion formula for correcting said first crop information based on said second crop information;

measuring reflectivity of light from unknown crop in said same plant field, whose wavelengths of light have relation to crop information which increases or decreases depending on growth of crop;

obtaining said first crop information of said unknown crop by applying said measured reflectivity of said unknown crop to said first crop related formula;

obtaining third crop information by correcting said first crop information of said unknown crop by division by division based on said compensation conversion formula; and determining the nutritious condition of said unknown crop in said plant field based on said corrected third crop information.

12. A method of diagnosing nutritious condition of crop in a plant field according to claim 11, in which said first crop information is obtained for each unit plant field.

13. A method of diagnosing nutritious condition of crop in a plant field according to claim 11, in which said first crop information is obtained for each arbitrarily predetermined unit area of a plant field smaller than a unit plant field.

14. A method of diagnosing nutritious condition of crop in a plant field according to claim 11, in which said first crop related formula and compensation conversion formula are stored, the reflectivity is measured from a leaf blade of crop in an unknown plant field, and said third crop information is obtained based on said first crop related formula and said compensation conversion formula.

15. A method of diagnosing nutritious condition of crop in a plant field according to claim 11, one of said two divisions is a division which has shown a maximum value and the other of said two divisions is a division which has shown a minimum value.

16. A method of diagnosing nutritious condition of crop in a plant field according to claim 14, one of said two divisions is a division which has shown a maximum value and the other of said two divisions is a division which has shown a minimum value.

17. A method of diagnosing nutritious condition of crop in a plant field according to claim 14, in which said crop information is an amount of nitrogen content.

18. A method of diagnosing nutritious condition of crop in a plant field according to claim 11, in which said crop information is an amount of nitrogen content.

19. A method of diagnosing nutritious condition of crop in a plant field according to claim 14, in which said crop information is a leaf blade color.

20. A method of diagnosing nutritious condition of crop in a plant field according to claim 11, in which said crop information is a leaf blade color.

21. A method of diagnosing nutritious condition of crop in a plant field according to claim 14, in which, for measuring the reflectivity of light whose wave-lengths having relation to the crop information which increases or decreases depending on growth of crop, the reflection light of the crop is image taken by an image-taking means having a plurality of pixels, only the pixels having received the reflection light corresponding to the crop are selected and, based on the data of the light received of the selected pixels, said first crop information is obtained.

22. A method of diagnosing nutritious condition of crop in a plant field according to claim 11, in which, for measuring the reflectivity of light whose wave-lengths having relation to the crop information which increases or decreases depending on growth of crop, the reflection light of the crop is image taken by an image-taking means having a plurality of pixels, only the pixels having received the reflection light corresponding to the crop are selected and, based on the data of the light received of the selected pixels, said first crop information is obtained.

23. A method of diagnosing nutritious condition of crop in a plant field under exposure to natural light, said method comprising the steps of:

measuring reflectivity of light which comes from a predetermined crop of each division in said plant field that is divided into a plurality of divisions and whose wavelengths have relation to crop information which increases or decreases depending on growth of crop;

obtaining first crop information of said predetermined crop for each division by applying said reflectivity for each division to a first crop related formula established in advance for obtaining crop information from reflectivity, and storing said first crop information for each division;

selecting the first crop information of at least two divisions among said plurality of divisions;

irradiating a leaf blade of said predetermined crop in said selected two divisions, and measuring light amount of at least either one of transmitted light and reflected light whose wavelengths have relation to crop information which increases or decreases depending on growth of crop;

obtaining second crop information of said predetermined crop in said selected two divisions by applying said measured light amount for each division to a second crop related formula established in advance for obtaining crop information from light amount, and storing said second crop information for said selected two divisions;

determining a compensation conversion formula for correcting said first crop information based on said second crop information;

measuring reflectivity of light from unknown crop in said same plant field, whose wavelengths of light have relation to crop information which increases or decreases depending on growth of crop;

obtaining said first crop information of said unknown crop by applying said measured reflectivity of said unknown crop to said first crop related formula;

obtaining third crop information by correcting said first crop information of said unknown crop by division by division based on said compensation conversion formula; and determining the nutritious condition of said unknown crop in said plant field based on said corrected third crop information.

24. A method of diagnosing nutritious condition of crop in a plant field according to claim 23, in which said one division corresponds to a unit plant field.

25. A method of diagnosing nutritious condition of crop in a plant field according to claim 23, in which said plurality of divisions are defined in a unit plant field.

26. A method of diagnosing nutritious condition of crop in a plant field according to claim 23, in which said first crop related formula and compensation conversion formula are stored, the reflectivity is measured from a leaf blade of crop in an unknown plant field, and said third crop information is obtained based on said first crop related formula and said compensation conversion formula.

27. A method of diagnosing nutritious condition of crop in a plant field according to claim 26, one of said two divisions is a division which has shown a maximum value and the other of said two divisions is a division which has shown a minimum value.

28. A method of diagnosing nutritious condition of crop in a plant field according to claim 26, in which said crop information is an amount of nitrogen content.

29. A method of diagnosing nutritious condition of crop in a plant field according to claim 26, in which said crop information is a leaf blade color.

30. A method of diagnosing nutritious condition of crop in a plant field according to claim 26, in which, for measuring the reflectivity of light whose wavelengths having relation to the crop information which increases or decreases depending on growth of crop, the reflection light of the crop is image taken by an image-taking means having a plurality of pixels, only the pixels having received the reflection light corresponding to the crop are selected and, based on the data of the light received of the selected pixels, said first crop information is obtained.

31. A method of diagnosing nutritious condition of crop in a plant field according to claim 23, one of said two divisions is a division which has shown a maximum value and the other of said two divisions is a division which has shown a minimum value.

32. A method of diagnosing nutritious condition of crop in a plant field according to claim 23, in which said crop information is an amount of nitrogen content.

33. A method of diagnosing nutritious condition of crop in a plant field according to claim 23, in which said crop information is a leaf blade color.

34. A method of diagnosing nutritious condition of crop in a plant field according to claim 23, in which, for measuring the reflectivity of light whose wave-lengths having relation to the crop information which increases or decreases depending on growth of crop, the reflection light of the crop is image taken by an image-taking means having a plurality of pixels, only the pixels having received the reflection light corresponding to the crop are selected and, based on the data of the light received of the selected pixels, said first crop information is obtained.

* * * * *